(12) United States Patent
Komatsu (10) Patent No.: US 8,777,366 B2
(45) Date of Patent: Jul. 15, 2014

(54) LIQUID-DISCHARGING DEVICE, AND METHOD FOR SUBSTITUTING LIQUID

(71) Applicant: Seiko Epson Corporation, Tokyo (JP)

(72) Inventor: Shinya Komatsu, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 13/785,676

(22) Filed: Mar. 5, 2013

(65) Prior Publication Data

US 2013/0235113 A1    Sep. 12, 2013

(30) Foreign Application Priority Data

Mar. 7, 2012 (JP) .................... 2012-050736

(51) Int. Cl.
  B41J 29/393 (2006.01)
  B41J 29/38 (2006.01)
  B41J 2/165 (2006.01)
  B41J 2/175 (2006.01)
  B41J 2/045 (2006.01)
  G01N 27/22 (2006.01)

(52) U.S. Cl.
  CPC ............. *B41J 2/16547* (2013.01); *B41J 2/175* (2013.01); *B41J 2/04571* (2013.01); *G01N 27/22* (2013.01)
  USPC ............................................... 347/19; 347/6

(58) Field of Classification Search
  CPC .... B41J 2/16547; B41J 2/04571; B41J 2/175; G01N 27/22; G01N 2291/0281
  USPC ............. 347/6, 7, 19, 68, 74, 76, 84, 85
  See application file for complete search history.

(56) References Cited

U.S. PATENT DOCUMENTS

| 7,182,420 B2 * | 2/2007 | Nakazawa | 347/7 |
| 7,370,923 B2 * | 5/2008 | Tanno et al. | 347/7 |
| 2012/0251147 A1 * | 10/2012 | Gomi et al. | 399/58 |

FOREIGN PATENT DOCUMENTS

JP    2010-105286 A    5/2010

* cited by examiner

*Primary Examiner* — An Do
(74) *Attorney, Agent, or Firm* — Global IP Counselors, LLP (57) ABSTRACT

A liquid-discharging device includes a nozzle that discharges liquid including a substance having sedimentation properties, a liquid supply channel, an inspection part, stirring part and a control part. The inspection part brings the liquid to be discharged from the nozzle to a first electric potential by a first electrode, discharges the liquid toward a second electrode of a second electric potential, and inspects a discharge state of the liquid based on a change of an electrostatic capacitance between the first electrode and the second electrode. The control part causes the nozzle to eject the liquid in order to substitute the liquid in an area downstream side than a predetermined area with the liquid stirred by the stirring part in the predetermined area. The control part determines a timing of ejection completion of the liquid based on the change of the electrostatic capacitance.

5 Claims, 10 Drawing Sheets

LIQUID-DISCHARGING DEVICE, AND METHOD FOR SUBSTITUTING LIQUID

CROSS-REFERENCE TO RELATED APPLICATIONS

This application claims priority to Japanese Patent Application No. 2012-050736 filed on Mar. 7, 2012. The entire disclosure of Japanese Patent Application No. 2012-050736 is hereby incorporated herein by reference.

BACKGROUND

1. Technical Field

The present invention relates to a liquid-discharging device, and a method for substituting liquid.

2. Related Art

As a liquid-discharging device, an inkjet printer is known to form an image on a medium by discharging ink, which is liquid type ink, from a head. In this type of printer, it is proposed that ink which is discharged from a nozzle is changed by switching ink which is supplied to the nozzle of the head (see e.g., Japanese Laid-Open Patent Publication No. 2010-105286).

SUMMARY

In a printer, there is a case that uses an ink including a substance having sedimentation properties such as color materials (e.g., pigments). In this case, the substance having sedimentation properties in the ink is precipitated in an ink passage (ink supply pipe, or the like) from an ink cartridge to a head so that there is a possibility that ink is divided into a high concentration part and a low concentration part. In this case, ink in a predetermined area of the ink supply pipe can be stirred and it can be substituted by ink which is downstream side of the ink supply direction.

Conventionally, when a substitution was performed, an ink ejection amount was determined with the consideration of an error so that the stirred ink (liquid) is surely discharged from the head (in other words, extra ink including the margin due to the error was ejected). However, in this case, even though the concentration was uniformed by stirring, there was a possibility that the amount of ink which was ejected (discarded) was increased without using it for a print.

In view of this, an object of the present invention is to surely perform a substitution and reduce an ejected liquid amount by the substitution.

A liquid-discharging device according to one aspect includes a nozzle, a liquid supply channel, an inspection part, a stirring part, and a control part. The nozzle is configured and arranged to discharge liquid including a substance having sedimentation properties. The liquid supply channel is configured and arranged to supply the liquid to the nozzle from a liquid tank that stores the liquid. The inspection part is configured and arranged to bring the liquid to be discharged from the nozzle to a first electric potential by a first electrode, to discharge the liquid toward a second electrode of a second electric potential which is different from the first electric potential, and to inspect a discharge state of the liquid based on a change of an electrostatic capacitance between the first electrode and the second electrode. The stirring part is configured and arranged to stair the liquid in a predetermined area of the liquid supply channel. The control part is configured and arranged to cause the nozzle to eject the liquid in order to substitute the liquid in an area downstream side than the predetermined area with respect to a liquid supply direction with the liquid stirred by the stirring part in the predetermined area. The control part is configured to determine a timing of ejection completion of the liquid based on the change of the electrostatic capacitance detected by the inspection part.

Other characteristics of the present invention are made apparent by the present specification and the descriptions of the accompanying drawings.

BRIEF DESCRIPTION OF THE DRAWINGS

Referring now to the attached drawings which form a part of this original disclosure.

DETAILED DESCRIPTION OF EXEMPLARY EMBODIMENTS

At least the following matters are made apparent by the present specification and the descriptions of the accompanying drawings.

A liquid-discharging device according to one embodiment includes a nozzle, a liquid supply channel, an inspection part, a stirring part, and a control part. The nozzle is configured and arranged to discharge liquid including a substance having sedimentation properties. The liquid supply channel is configured and arranged to supply the liquid to the nozzle from a liquid tank that stores the liquid. The inspection part is configured and arranged to bring the liquid to be discharged from the nozzle to a first electric potential by a first electrode, to discharge the liquid toward a second electrode of a second electric potential which is different from the first electric potential, and to inspect a discharge state of the liquid based on a change of an electrostatic capacitance between the first electrode and the second electrode. The stirring part is configured and arranged to stair the liquid in a predetermined area of the liquid supply channel. The control part is configured and arranged to cause the nozzle to eject the liquid in order to substitute the liquid in an area downstream side than the predetermined area with respect to a liquid supply direction with the liquid stirred by the stirring part in the predetermined area. The control part is configured to determine a timing of ejection completion of the liquid based on the change of the electrostatic capacitance detected by the inspection part.

According to such a liquid-discharge device, it is possible that the completion of substitution is accurately detected, the substitution is properly performed, and an ejection amount of liquid is reduced.

In the liquid-discharge device, the control part is preferably configured to estimate a viscosity of the liquid based on the change of the electrostatic capacitance, and to determine the timing of ejection completion of the liquid based on a result of estimation.

According to such a liquid-discharge device, a timing of the completion of the liquid (substitution completion) can be detected with high accuracy from the estimated result of the viscosity.

In the liquid-discharge device, the substance having sedimentation properties may include a pigment. For example, white pigment is easily precipitated, and this is particularly effective in this case.

In the liquid-discharge device, the control part is preferably configured to cause the nozzle to eject the liquid by suctioning.

According to such liquid-discharge device, it can be easy to control the ejection amount of the liquid from the nozzle.

A method according to the embodiment is a method for substituting liquid in a liquid-discharge device including a nozzle configured and arranged to discharge the liquid including a substance having sedimentation properties, and a liquid supply channel configured and arranged to supply the liquid to the nozzle from a liquid tank that stores the liquid. The method for substituting liquid includes: stirring the liquid in a predetermined area of the liquid supply channel; ejecting the liquid from the nozzle in order to substitute the liquid in an area downstream side than the predetermined area with respect to a liquid supply direction with the liquid stirred in the predetermined area; inspecting a change of an electrostatic capacitance between a first electrode and a second electrode by bringing the liquid to be discharged from the nozzle to a first electric potential by the first electrode and discharging the liquid toward the second electrode of a second electric potential which is different from the first electric potential; and determining a timing of ejection completion of the liquid based on the change of the electrostatic capacitance.

In the embodiment below, an inkjet printer (hereinafter referred to as printer 1) is explained as an example of the liquid-discharging device.

Configuration of Printer

Figure 1A:
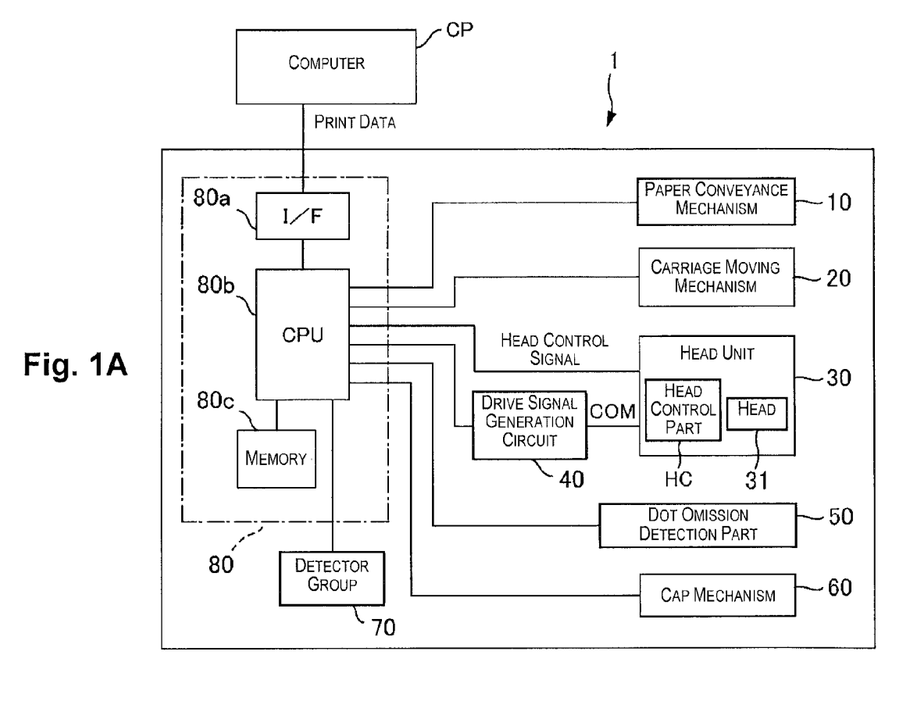
FIG. 1A is a block diagram describing a printing system which has a printer 1 and a computer CP.
Figure 1B:
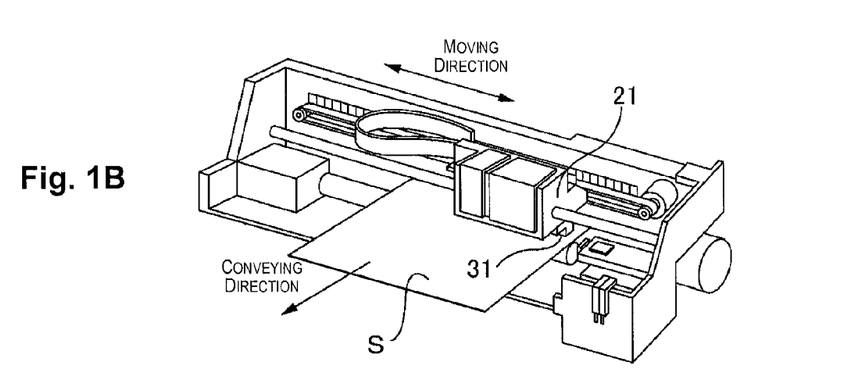
FIG. 1B is a perspective view of a printer 1.

FIG. 1A is a block diagram describing the print system having a printer 1 and a computer 1. FIG. 1B is a perspective view of the printer 1. The printer 1 discharges ink, which is a kind of liquid, to a medium such as a paper, a fabric, a film. The computer CP is connected to the printer 1 for the communication. To print an image by the printer 1, the computer CP sends a print data to the printer 1 in response to the image. The printer 1 comprises a paper conveyance mechanism 10, a carriage moving mechanism 20, a head unit 30, a drive signal generation circuit 40, a dot omission detector 50, a cap mechanism 60, detector group 70, and a controller 80.

In the paper conveyance mechanism 10, a medium (paper) is conveyed in a conveying direction. In the carriage moving mechanism 20, a carriage 21 which attaches with a head unit 30, is moved in a moving direction (a direction intersects with the conveying direction).

The head unit 30 has a head 31 and a head control part HC. The head 31 discharges ink toward a paper. The head control part HC controls the head 31 based on a head control signal from the controller 80 of the printer 1.

Figure 2A:
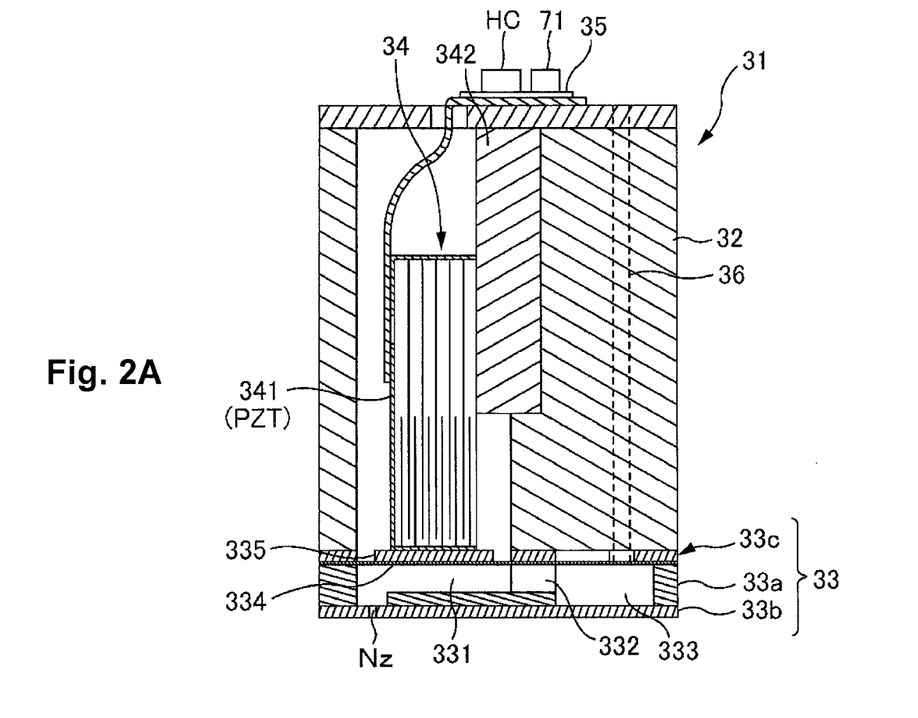
FIG. 2A is a cross-sectional view of a head 31.

FIG. 2A shows a cross-sectional view of the head 31. The head 31 has a case 32, a flow channel unit 33, and a piezo element unit 34. The case 32 stores a piezo element PZT and the like and is used as a fixation member. For example, it is made by non-conductive resin material such as epoxy resin.

The flow channel unit 33 has a flow channel formative substrate 33a, a nozzle plate 33b, and a vibrating plate 33c. The nozzle plate 33b is connected on one side surface of the flow channel formative substrate 33a and the vibrating plate 33c is connected on the other surface. In the flow channel formative substrate 33a, a pressure chamber 331, an ink supply opening 332, and an opening part and a channel of a common ink chamber 333 are formed. The flow channel formative substrate 33a is made by, for example, a silicon substrate. Also, in the common ink room 333, ink is supplied from an ink cartridge 100 (corresponding to a liquid tank) through the ink supply pipe 36.

In the nozzle plate 33b, a nozzle group which is formed by a plurality of nozzles Nz, is provided. The nozzle plate 33b is made by a plate member having a conductive property, e.g., a thin metal plate. Also, the nozzle plate 33b is connected to a ground line so as to become a ground electrical potential. In a part corresponding to each pressure chamber 331 in the vibrating plate 33c, a diaphragm part 334 is provided. The diaphragm part 334 is deformed by a piezo element PZT so that a volume of the pressure chamber 331 is changed. By the way, a vibrating plate 33c, an adhesive layer, or the like is interposed so that the piezo element PZT and the nozzle plate 33b are electrically in an insulated condition.

The piezo element unit 34 has a piezo element group 341 and a fixation plate 342. The piezo element group 341 has a ctenidium shape. Each one of ctenidium is the piezo element PZT. An apical surface of each piezo element PZT is bonded on an insular part having the corresponded diaphragm part 334. The fixation plate 342 supports the piezo element group 341 and becomes a mounting part for the case 32. The piezo element PZT is a kind of an electric machine transformation device, and when a drive signal COM is applied, it stretches in a longer direction so that the pressure change is given to the liquid in the pressure chamber 331. The pressure change for ink in the pressure chamber 331 occurs due to volumetric change of the pressure chamber 331. By using the pressure change, ink droplet can be discharged from the nozzles Nz.

Figure 2B:
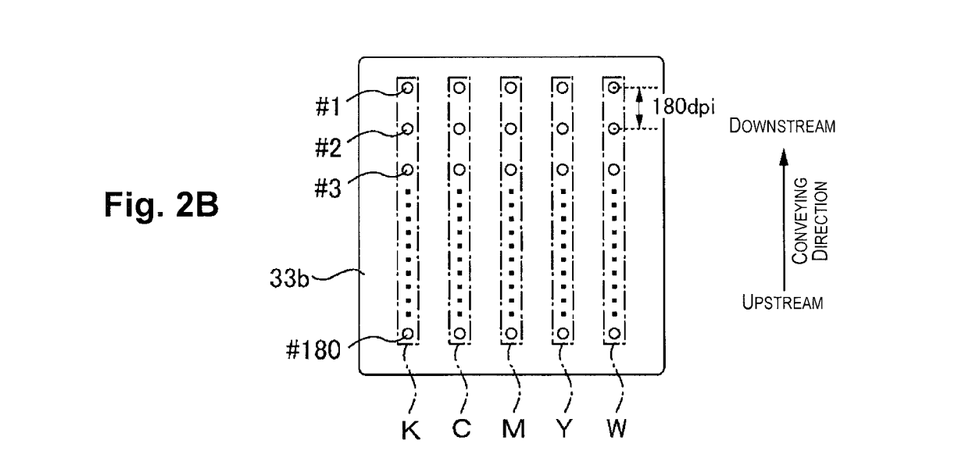
FIG. 2B is an illustration showing an arrangement of nozzles provided in a nozzle plate 33b.

FIG. 2B shows an arrangement of the nozzles (Nz) provided in the nozzle plate 33b. In the nozzle plate, a plurality of nozzle lines which lines 180 nozzles (#1 to #180) is arranged at certain intervals of 180 dpi along the conveyance direction of a paper. Each nozzle line discharges different color inks, respectively, and there are 5 nozzle lines in the nozzle plate 33b. Concretely, they are a black ink nozzle line K, a cyan ink nozzle line C, a magenta ink nozzle line M, a yellow ink nozzle line Y, and a white ink nozzle line W.

By the way, in the present embodiment, the white ink discharged from the white ink nozzle line W is, for example, ink for printing a background color (white) of the color image when printing on a transparent medium. Because of this, a color image is more visible by making white color on the background. By the way, the white ink includes a white pigment (corresponding to a sedimentation property material) as a color material. As a white pigment, for example, it can be a metallic oxide, a barium sulfate, a calcium carbonate, or the like. As a metallic oxide, for example, it can be titanium dioxide, zinc oxide, silica, alumina, magnesium oxide, or the like. Among these materials, in view of excellent whiteness, it is preferable to use titanium dioxide. The white ink is easy to increase viscosity and become solidified when it is left for a long time. Also, the pigment is easy to settle out when it is left for a long time.

A drive signal generation circuit 40 generates a drive signal COM. When the drive signal COM is applied to the piezo element PZT, the piezo element PZT stretches so that it changes the volume of the pressure chamber 331 corresponding to each nozzle Nz. At the time of printing or the dot omission inspection, the drive single COM is applied to the head 31 when it is a flushing as a recovery operation of the dot omission nozzles Nz.

A dot omission detection part 50 (corresponding to an inspection part) inspects a discharge state of ink from each nozzle Nz. A cap mechanism 60 controls evaporation of ink solvent from the nozzles Nz, and performs a suctioning operation to suction ink from each nozzle Nz to recover a discharge ability of the nozzles Nz. A detector group 70 configures a plurality of detectors that observe a status of the printer 1. The results of these detectors are outputted to a controller 80.

The controller 80 (corresponding to a control part) entirely controls the printer 1. The controller 80 has an interface part 80a, a CPU 80b, and a memory 80c. The interface 80a delivers and receives data with the computer CP. The memory 80c secures a storage area or an operation area for computer programs. The CPU 80b controls each control target part (the paper conveyance mechanism 10, the carriage moving mechanism 20, the head unit 30, the drive signal generation circuit 40, the dot omission detection part 50, the cap mechanism 60, and the detector group 70) in accordance with the computer programs stored in the memory 80c.

In such printer 1, the controller 80 moves carriage 21 in a moving direction and continuously discharges ink from the head 31 so that a dot forming process that forms dots on a paper and a conveyance process that conveys a paper in the conveying direction are repeatedly executed. As a result, dots are formed in the position different from the position of the dots formed by the dot forming process so that two-dimensional image is printed on the medium.

Discharge Inspection and Recovery Operation

When ink (liquid) is not discharged from the nozzles for a long time, or when a foreign substance such as a paper dust is adhered, the nozzles may be clogged. When the nozzles are clogged, ink is not discharged at the time that the ink should be discharged so that there is a phenomenon that dots are not formed (dot omission) in a part that the dots should be formed. When the "dot omission" occurs, the image quality is deteriorated. Thus, in the present embodiment, as a result of "discharge inspection" performed by the dot omission detection part 50, when a dot omission nozzle is detected, by performing "recovery operation", ink can be properly discharged from the dot omission nozzle.

By the way, the dot omission inspection may be performed immediately after the power in the printer 1 is turned on or when the printer 1 starts printing at the time of receiving the print data from the computer CP. Also, the dot omission inspection may be performed in a predetermined period of time while printing for a long time. Hereinafter, after explaining about a recovery operation of a dot omission nozzle, the discharge inspection (brief summary) will be explained.

Recovery Operation

Figure 3A:
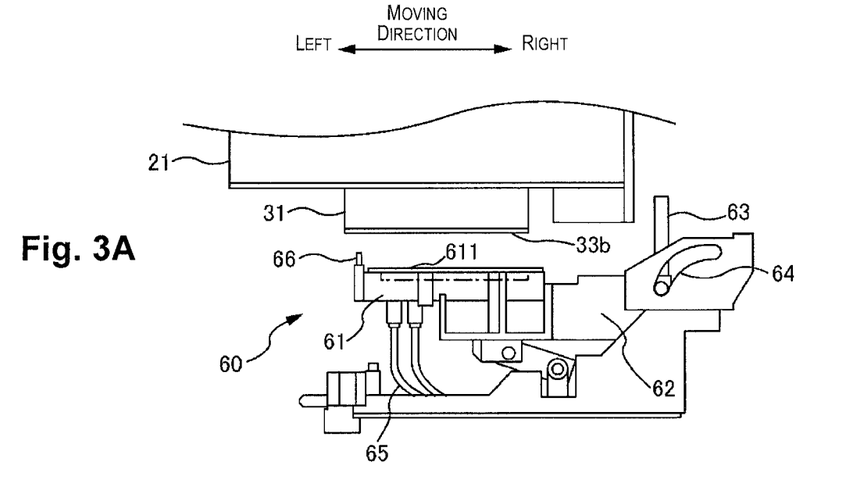
FIGS. 3A to 3C show an illustration showing a positional relationship between the head 31 and a cap mechanism 60 when performing a recovery operation.
Figure 3B:
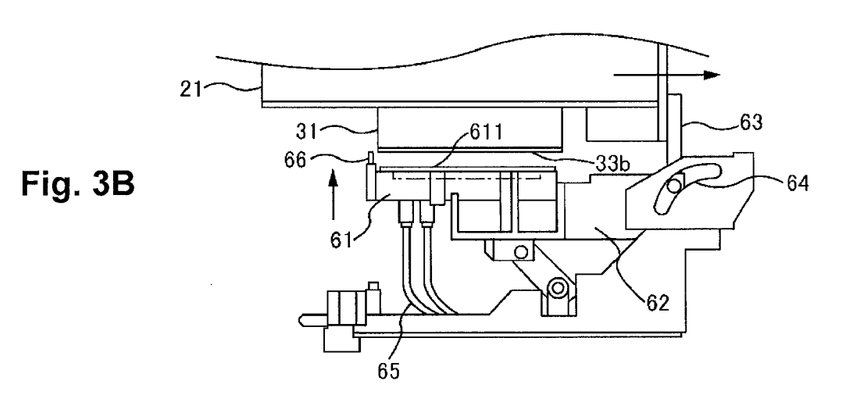
Figure 3C:
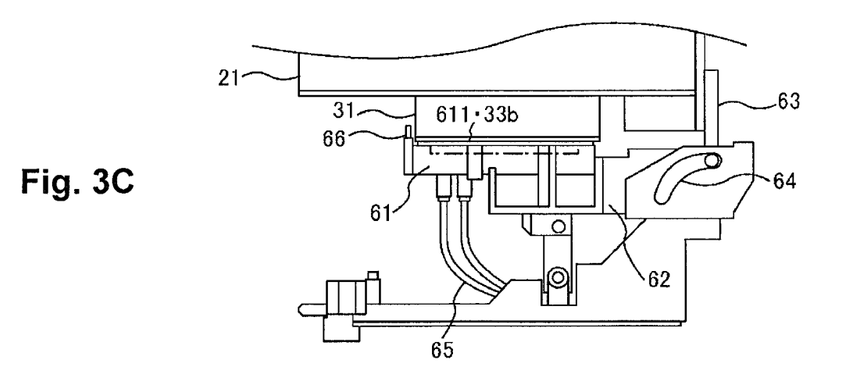

FIGS. 3A to 3C show a position relationship between the head 31 and the cap mechanism 60 at the time of a recovery operation. First, the cap mechanism will be explained. The cap mechanism 60 has a cap 61 and a slider member that is movable in an obliquely up and down direction with supporting the cap 61. The cap 61 has a rectangular shape basilar part (not shown in the drawing) and a side wall portion 611 that stands from peripheral border of the basilar part. It has a thin box shape which opens an upper surface opposing to the nozzle plate 33b. A sheet-shaped moisturizing member made by a porous material such as a felt, a sponge, or the like is arranged in a space surrounded by the basilar part and the side wall portion 611.

As shown in FIG. 3A, in a condition that the carriage 21 is off from a home position (right side of the moving direction, specifically, it is a position of FIG. 3C described later), the cap 61 is adequately arranged in a lower position than the surface of the nozzle plate 33b (hereinafter referred to as nozzle surface). And, as shown in FIG. 3B, when the carriage 21 moves to the home position side (right side of the drawing), the carriage 21 is abutted to the abutting part 63 provided on the slider member 62, and the abutting part 63 moves to the home position side with carriage 21. When the abutting part 63 moves to the home position side, the slider member 62 goes up along a long hole 64 for a guide. Finally, as shown in FIG. 3C, when the carriage 21 is located in the home position, the wall side 611 of the cap 61 (porous component) and the nozzle plate 33b are attached. Therefore, by positioning the carriage 21 in the home position at the time of the power off or a long period of pausing, the evaporation of ink solvent from the nozzles can be suppressed.

Next, the recovery operation will be explained. There is a "flushing operation" as one of recovery operations of the dot omission nozzle. As shown in FIG. 3B, the flushing operation is an operation to eliminate clogging of the nozzles by forcibly and continuously discharging ink droplet from each nozzle in a condition that a small gap is opened between the nozzle surface and opening edge of the cap 61.

Also, in a space between the bottom surface of the cap 61 and the side wall part 611, a waste fluid tube 65 is connected, and in a middle of the waste fluid tube 65, a suction pump is connected (not shown in the drawing). As another one of the recovery operations, as shown in FIG. 3C, the "pump suction" is performed in a state that the opening edge of the cap 61 contacts to the nozzle surface. In a condition that the side wall part 611 of the cap 61 and the nozzle surface are attached, when the suction pump is operated, the space of the cap 61 can be negative pressure. Because of this, ink in the head 31 can be suctioned with the thick viscosity ink or paper dust, and the dot omission nozzle can be recovered.

Other than that, the cap mechanism 60 is maintained in a position as shown in FIG. 3B. By moving the carriage 21 in a moving direction and by a wiper 66 upwardly projected than the side wall part 611 of the cap 61, the ink droplet or the foreign matter adhered on the nozzle surface can be excluded. As a result, ink can be properly discharged from the nozzle clogged by the foreign matter.

Dot Omission Detection Part 50

Figure 4:
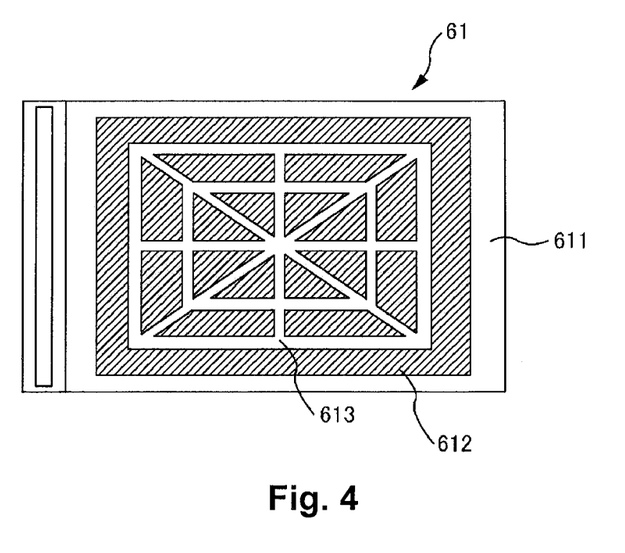
FIG. 4 shows a top view of a cap 61.
Figure 5A:
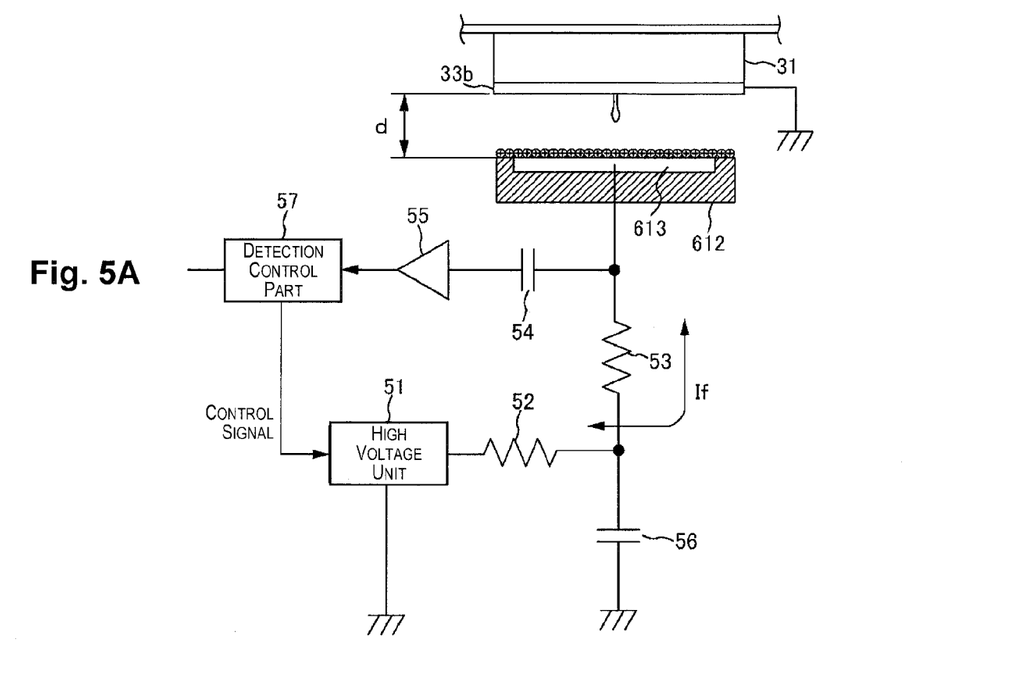
FIG. 5A is an illustration explaining a dot omission detector 50.
Figure 5B:
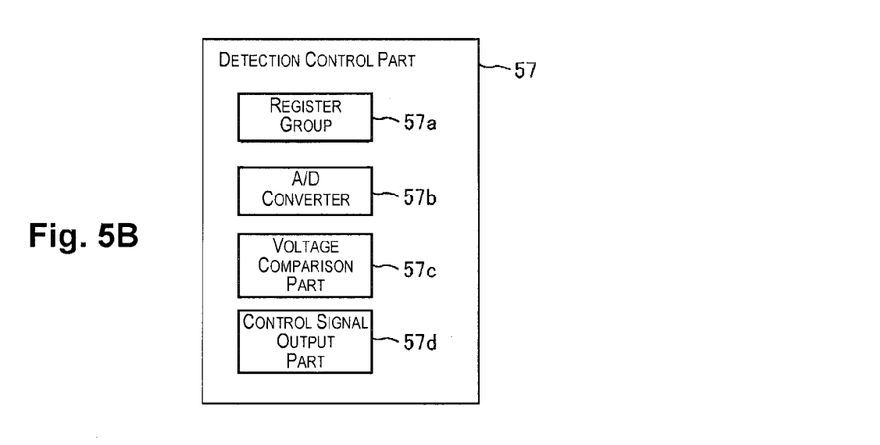
FIG. 5B is a block diagram explaining an inspection control 57 of the dot omission detector 50.

FIG. 4 is a top view of the cap 61. FIG. 5A is an explanatory diagram of the dot omission detection part 50. FIG. 5B is a block diagram describing the detection control part 57 of the dot omission detection part 50. The dot omission detection part 50 actually discharges ink from each nozzle, and detects a discharge state of ink such as whether ink was properly discharged. First, the configuration of the dot omission detection part 50 will be explained. As shown in FIG. 5A, the dot omission detection part 50 has a high-voltage power supply unit 51, a first restricted resistance 52, a second restricted resistance 53, a condenser for detection 54, an amplifier 55, a smoothing condenser 56, and the detection control part 57.

As shown in FIG. 3B and FIG. 5A, at the time of the dot omission detection, the nozzle surface and the cap 61 is opposed in a space with a predetermined distance d. In a space surrounded by the cap 61 and the side wall part 611, the moisturizing member 612 and the wire-shaped electrode for detection 613 are arranged as shown in FIG. 4. The electrode for detection 613 becomes high potential of approximately 600V to 1 kV at the time of the dot omission detection operation. The electrode 613 for detection illustrated in FIG. 4 has a frame part provided as a double rectangular shape, a diagonal line part that connects diagonal portions of the frame, and a cross part that connects at a middle point in each side of the frame part. By this configuration, it is uniformly charged over a wide range. Also, the ink solvent of the present embodiment is liquid having conductive property (for example, water), and when the electrode for detection 613 becomes high electric potential in a condition that the moisturizing member 612 is wet, the surface of the moisturizing member 612 becomes the same electric potential. In this point, also, the area where ink is discharged from the nozzle is uniformly charged over a wide range.

The high-voltage power supply unit 51 is a kind of a power source that makes the electrode for detection 613 in the cap 61 to be a predetermined electric potential. The high-voltage power source unit 51 of the present embodiment is configured by the DC power source of approximately 600V to 1 kV, and the operation is controlled by a control signal from the detection control part 57.

The first restricted resistance 52 and the second restricted resistance 53 are arranged between the output terminal of the high-voltage power source unit 51 and the electrode for detection 613, and the current that flows between the high-voltage power source unit 51 and the electrode for detection 613 is restricted. In the present embodiment, the first restricted resistance 52 and the second restricted resistance 53 are the same resistance value (e.g., 1.6 MΩ), and the first restricted resistance 52 and the second restricted resistance 53 are connected in series. As shown in the drawing, one end of the first restricted resistance 52 is connected to the output terminal of the high-voltage power source unit 51, and another end is connected to one end of the second restricted resistance 53. Another end of the second restricted resistance 53 is connected to the electrode for detection 613.

The condenser for detection 54 is an element for extracting an electronic potential change component of the electrode for detection 613, and one end is connected to the electrode for detection 613 and another end is connected to the amplifier 55. To this place, the condenser for detection 54 is interposed so that a bias component (DC component) of the electrode for detection 613 can be excluded and it can facilitate to handle a signal. In the present embodiment, the capacity of the condenser for detection 54 is 4700 pF.

The amplifier 55 amplifies a signal (change in electric potential), which appears in another end of the condenser for detection 54, and outputs the signal. In the amplifier 55 of the present embodiment, it is configured that the gain becomes 4000 times. Because of this, the change component of the electric potential having a variation range of approximately 2 to 3V can be obtained as a voltage signal. A group of the condenser for detection 54 and the amplifier 55 corresponds to a kind of a detector, and an electrical change in the electrode for detection 613 that occurs by the discharge of ink droplet is detected.

The smoothing conductor 56 controls acute change of an electric potential. One end of the smoothing condenser 56 of the present embodiment connects to a signal line which connects between the first restricted resistance 52 and the second restricted resistance 53, and another end is connected to the ground. In this embodiment, the capacity of the smoothing condenser 56 is 0.1 µF.

The detection control part 57 is a part that controls the dot omission detection part 50. As shown in FIG. 5B, the detection control part 57 has a register group 57a, an AD converter 57b, an electric voltage comparison part 57c, and a control signal output part 57d. The register group 57a is configured by a plurality of registers. In each register, a judgment result of each nozzle Nz or a voltage threshold for a judgment is stored. The AD converter 57b converts a voltage signal (analog value), which was amplified and outputted from the amplifier 55, to a digital value. The voltage comparison part 57c compares a size of an amplitude value based on a voltage signal, which was amplified, with an electric voltage threshold. The control signal output part 57d outputs a control signal to control an operation of the high-voltage power source unit 51.

Brief Summary of Discharge Inspection

In the printer 1, the nozzle plate 33b (corresponding to the first electrode) is connected to the ground to be a ground electric potential (corresponding to the first electric potential) so that the electrode for detection 613 (corresponding to the second electrode) arranged in the cap 61 becomes high electric potential of approximately 600V to 1 kV (corresponding to the second electric potential). By the nozzle plate of the ground electric potential, ink droplet discharged from a nozzle becomes the ground electric potential. The nozzle plate 33b and the electrode for detection 613 are opposed with a space in a predetermined distance d (see FIG. 5A), and ink droplet is discharged from a nozzle for a detection target. And, the detection control part 57 obtains a voltage signal SG through the condenser for detection 54 and the amplifier 55 by an electric change which occurs in the electrode for detection 613 side due to ink droplet discharge. Based on an amplitude value (change in an electric potential) in the voltage signal SG, the detection control part 57 judges an ink discharge state whether ink droplet is properly discharged from a detection target nozzle.

Principles of the detection are described as follows. By arranging the nozzle plate 33b and the electrode for detection 613 with a space in a predetermined distance d, it has configuration that these members are performed as a condenser. In other words, as shown in FIG. 5A, the nozzle plate 33b is connected to the ground, and by attaching the nozzle plate 33b, ink which extends to the nozzle Nz with column shape (hereinafter referred to as "ink column") becomes the ground electric potential. The elongation of the ink (length of the ink column) changes an electrostatic capacitance in the condenser. Specifically, by discharging ink from the nozzle, the ink of the ground electric potential and the electrode for detection 613 are configured as a condenser so as to change the electrostatic capacitance.

And, when the electrostatic capacitance becomes small, the charge amount that can be stored between the nozzle plate 33b and the electrode for detection 613 is reduced. Because of this, the charge of the surplus moves to the high-voltage power source unit 51 from the electrode for detection 613 through respective restricted resistances 52, 53. In other words, the current flows toward the high-voltage power source unit 51. On the other hand, when the electrostatic capacitance increases and reduces, or when the electrostatic capacitance returns, the charge moves to the electrode for detection 613 side from the high-voltage power source unit 51 through the respective restricted resistances 52, 53. In other words, the current flows toward the electrode for detection 613. When this kind of current (for convenience, it may be called as current for discharge inspection IF) flows, the electric potential of the electrode for detection 613 is changed. The electric potential change of the electrode for detection 613 also appears as an electric potential change of another electric conductor (electric conductor in the amplifier 55 side) in the condenser for detection 54. Accordingly, by observing the electric change of another electric conductor, it can judge a discharge state of the ink droplet.

Figure 6A:
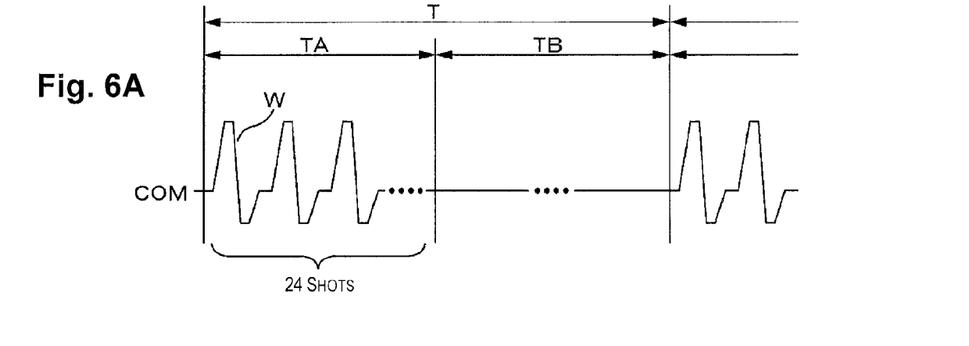
FIG. 6A is an illustration showing one example of a drive signal COM used at the time of a discharge inspection.
Figure 6B:
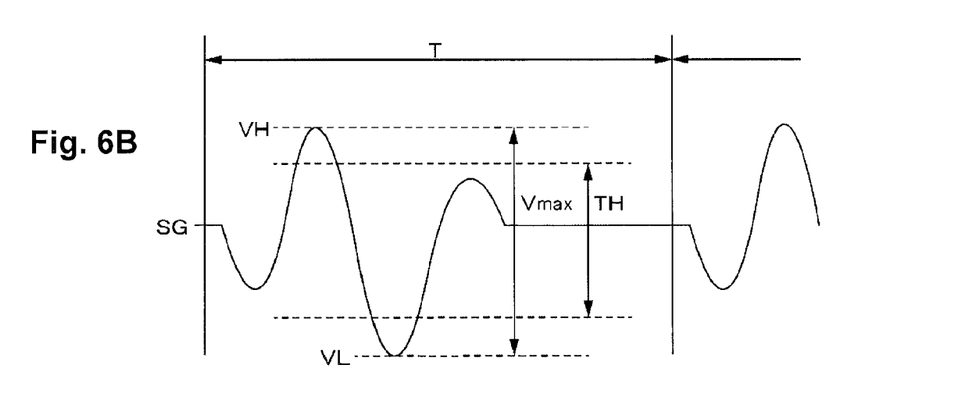
FIG. 6B is an illustration showing a description of a voltage signal SG outputted from an amplifier 55 when ink was discharged from the nozzles by the drive signal COM.
Figure 6C:
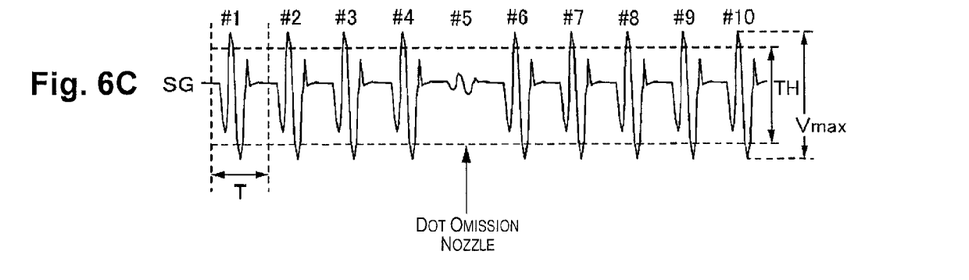
FIG. 6C is an illustration showing the voltage signal SG which is the discharge inspection result of the plurality of nozzles.

FIG. 6A shows one example of a drive signal COM used at the time of a discharge inspection. FIG. 6B shows a description of a voltage signal SG outputted from an amplifier 55 when ink was discharged from the nozzles by the drive signal COM. FIG. 6C shows a voltage signal SG which is the discharge inspection result of a plurality of nozzles (here, it is nozzles #1 to #10). The drive signal COM has a plurality of drive waveforms W (e.g., 24) to discharge ink from the nozzles at a first half period TA in a repeat period T, and in the second half period TB, the certain electric potential is maintained in an intermediate electric potential. The drive signal generation circuit 40 repeatedly generates a plurality of drive waveforms W (24 drive waveforms) every period T. This repeat period T corresponds to a required time for an inspection of one nozzle.

First, the drive signal COM is applied to the piezo element PZT, which corresponds to a nozzle to be inspected, over the repeat period T. Because of this, ink droplets are continuously discharged from the nozzle of the discharge inspection target in the first half period TA (e.g., 24 shots are discharged). Because of this, the electric potential of the electrode for detection 613 is changed, and the amplifier 55 outputs the electric potential change as a voltage signal SG (sine curve) as shown in FIG. 6B to the detection control part 57. By the way, the amplitude of the voltage signal SG by ink droplet for 1 shot is small so that by continuously discharging ink droplets from the nozzle, a voltage signal SG having enough amplitude for inspection is obtained.

The detection control part 57 calculates a maximum amplitude Vma x (difference between the maximum voltage VH and the minimum voltage VL) from the voltage signal SG in the inspection period (T) of the nozzle, which is the inspection target, and compares the maximum amplitude Vma x and a predetermined threshold TH. When ink is discharged from the nozzle, which is the inspection target, in response to the drive signal COM, the electric potential of the electrode for detection 613 is changed, and the maximum amplitude Vma x of the voltage signal SG becomes larger than the threshold TH. On the other hand, due to clogging, when ink is not discharged from the nozzle, which is the inspection target, or when the discharged ink is small amount, the electric potential of the electrode for detection 613 is not changed or the electric potential change is small so that the maximum amplitude Vma x of the voltage signal SG becomes less than the threshold TH.

After applying a drive signal COM to a piezo element PZT corresponding to a certain nozzle, a drive signal COM applies to a piezo element PZT corresponding to a nozzle, which is the next inspection target, over the repeat period T. As described, in each one nozzle of an inspection target, a drive signal COM applies to a piezo element PZT corresponding to the nozzle over the repeat period T. As a result, the detection control part 57 can obtain a voltage signal SG, which generates a sine curve of an electric potential change, in each repeat period T as shown in FIG. 6C.

For example, in the result of FIG. 6C, the maximum amplitude Vma x of the voltage signal SG corresponding to the nozzle #5 during the inspection period is less than the threshold value TH so that the detection control part 57 judges that the nozzle #5 is the dot omission nozzle. The maximum amplitude Vma x of the voltage signal SG corresponding to each inspection period of other nozzles (#1 to #4, #6 to #10) is more than the threshold value TH so that the detection control part 57 judges that other nozzles are a normal nozzle. By this, when the dot omission nozzle is detected by the detection control part 57, the controller 80 of the printer 1 executes recovery for the head 31. As a result, a high quality image can be printed without dot omission.

Relationship between Ink Viscosity and Length of Ink Column

Figure 7:
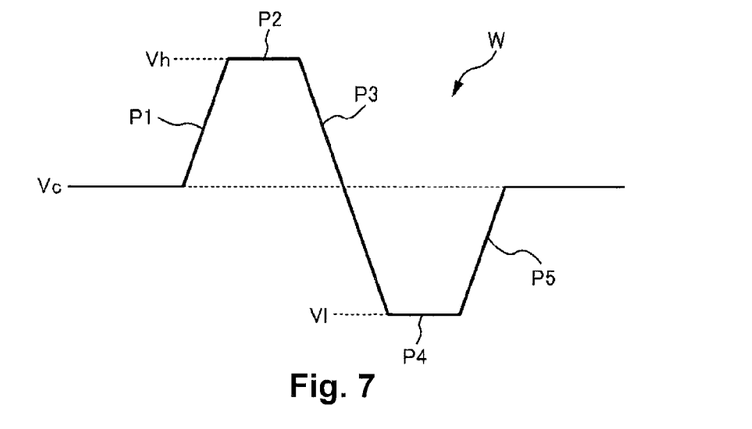
FIG. 7 is an illustration showing a drive waveform W generated by the drive signal COM for the inspection.
Figure 8:
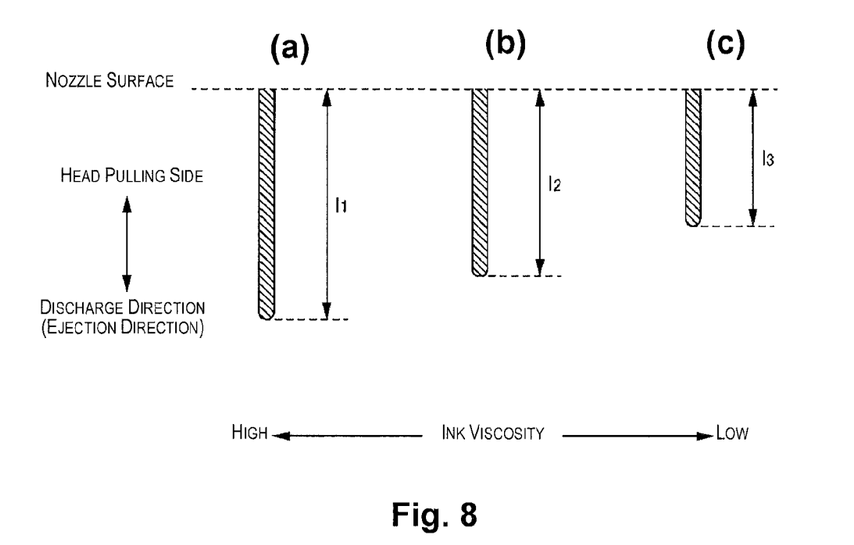
FIG. 8 is an explanatory diagram of a relationship between degree of ink viscosity and a length of an ink column.

FIG. 7 is an illustration showing a drive waveform W which is generated by a drive signal COM for detection (FIG. 6A). FIG. 8 is an explanatory diagram of a relationship between an ink viscosity and a length of an ink column. In FIG. 8, it shows that ink having a column shape is projected from a nozzle surface (lower surface of the nozzle plate 33b) of the head 31, and a shaded area in the drawings corresponds to ink. Also, an ink viscosity is reducing in the order of (a), (b) and (c) in FIG. 8.

First, the detail about a drive waveform W that is generated by a drive signal for detection COM will be explained. The drive waveform W has the first expansion element P1 that raises an electric potential from an intermediate electric potential Vc to the highest electric potential Vh, the first hold element P2 that maintains the highest electric potential Vh, a contractile element P3 that comes down the electric potential from the highest electric potential Vh to the lowest electric potential V1, the second hold element P4 that maintains the lowest electric potential V1, and the second expansion element P5 that raises the electric potential from the lowest electric potential V1 to the intermediate electric potential Vc.

The piezo element PZT does not stretch in a state that the intermediate electric potential Vc applies to the piezo element PZT (See FIG. 2A). A volume of the pressure chamber 331 (see FIG. 2A) at the time that the intermediate electric potential Vc applies to the piezo element PZT is a reference volume. After that, when the first expansion element P1 of the drive waveform W applies to the piezo element PZT, the piezo element PZT is contracted in the longitudinal direction and the volume of the pressure chamber 331 is expanded. And, when the first hold element P2 applies to the piezo element PZT, the contracted state of the piezo element PZT is maintained and accordingly, the expanded state of the pressure chamber 331 is also maintained. Next, when the contractile element P3 applies to the piezo element PZT, the piezo element PZT stretches at one stretch from the contracted state and the volume of the pressure chamber 331 is contracted at once. By contracting the pressure chamber 331, the ink pressure in the pressure chamber 331 increases dramatically so that an ink column is projected form a nozzle and the ink droplet flies in a discharging direction. After that, the second hold element P4 applies to the piezo element PZT so that the stretched state of the piezo element PZT and the expanded state of the pressure chamber 331 are maintained. At the end, when the second expansion element P5 applies to the piezo element PZT, the volume of the pressure chamber 331 returns to the reference volume.

When the contractile element P3 of the drive waveform W is contracted by the pressure chamber 331, as shown in FIG. 8, it becomes a state that ink is projected in a column-shape from a nozzle. After that, the tip portion of the ink column is separated from the ink column and it flies in a discharging direction. By the way, the tip portion of the ink column calls "main droplet", and a distance between a point that separates the tip portion (main droplet) and a nozzle surface (lower surface of the nozzle plate 33b) calls "amount of tailing". At the time of printing, by landing the main droplet which is separated from the ink column on a medium, the dots are formed. On the other hand, the remaining portion of the ink column after the tip portion (main droplet) was separated forms very little ink droplet (satellite) and returns to the pressure chamber 331.

By the way, in FIG. 8, it is the same as the drive waveform W (contractile element P3) that applies to the piezo element PZT, but the viscosity of the ink which is used is different. As shown in FIG. 8, the length of the ink column when the contractile element P3 applies to the piezo element PZT is varied by the viscosity of the ink. For example, a relationship of the lengths of the ink columns $l_1$, $l_2$, $l_3$ as shown in the drawings becomes that the viscosity of the ink in (a) in FIG. 8 is the highest and the viscosity of the ink in (c) in FIG. 8 is the lowest. In other words, the high ink viscosity of the ink in (a) in FIG. 8 will be that a high concentration and the low ink viscosity of the ink in (c) in FIG. 8 will be a low concentration.

Here, when ink including a pigment (corresponding to a substance having sedimentation properties) is used as the ink, the concentration of the ink may become uneven in a state that the ink is not discharged for a long time. Specifically, in a case that it is a white ink which uses an inorganic material such as a titanium dioxide as a pigment and a specific color ink such as metallic ink which has a metallic luster, there is a characteristic that the particles of the color component is easily settled out due to the heavy weight.

Figure 9:
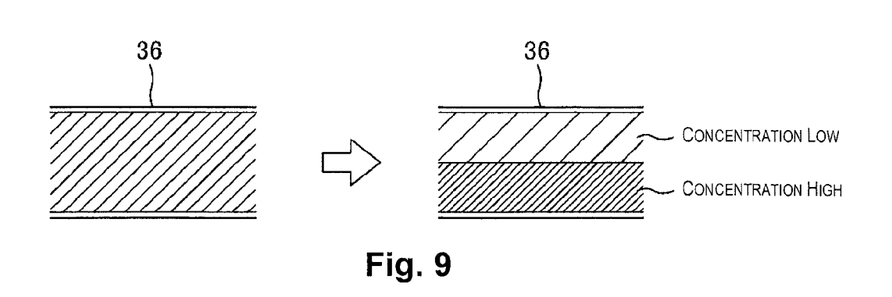
FIG. 9 is a cross-sectional view describing a change of an ink state in an ink supply channel.

FIG. 9 is a cross-sectional view describing a change of an ink state in an ink supply channel. In an example of this drawing, the ink supply pipe 36 that supplies ink to the nozzle of the head 31 is arranged in a perpendicular direction (horizontal direction of the drawing) to the vertical direction (up and down direction of the drawing). Also, in this case, a white ink including a white pigment is used as an ink. The diagonal lines of the drawing show an ink portion. Also, as the concentration of the ink becomes higher, the distance between the diagonal lines is narrow, and therefore, the line width (distance) of the diagonal lines is changed in response to the concentration of the ink. In the left side of the drawing in FIG. 9, the concentration in the ink supply pipe 36 is approximately-constant. However, when the time is elapsed in this state, the pigment is settled out and it becomes as the right side of FIG. 9. Specifically, a high concentration ink layer (thick) is formed in the lower side of the ink supply pipe 36, and an ink layer (supernatant layer) of a low concentration (thin) is formed in an upper side. More specifically, the concentration (in other words, viscosity) in the ink supply pipe 36 becomes uneven. Because of this, the amount and the concentration of the ink discharged from a nozzle become uneven so that the image quality deterioration may occur.

Thus, in the present embodiment, by stirring ink in the ink supply pipe 36, it is prevented from unevenness of the concentration.

Stirring

Figure 10:
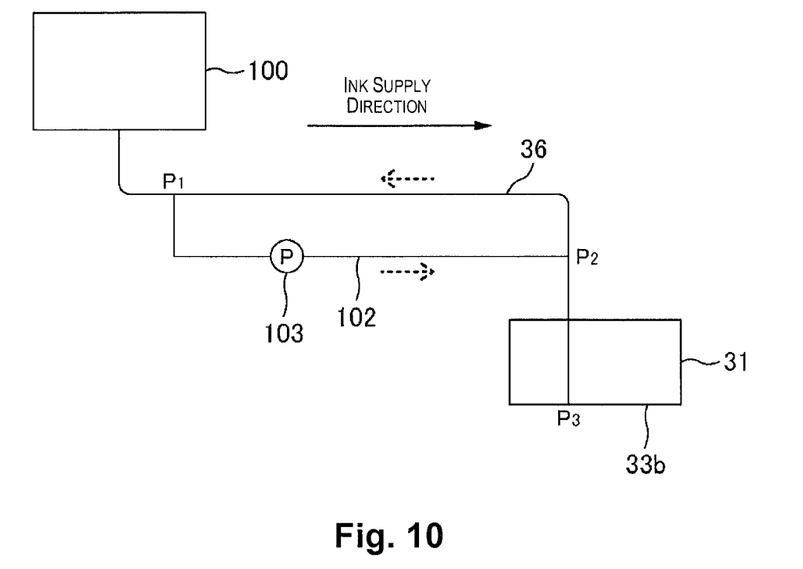
FIG. 10 is a schematic illustration of an ink supply channel to the head 31 in the present embodiment.

FIG. 10 is schematic illustration of an ink supply channel to the head 31 in the present embodiment. By the way, FIG. 10 simply shows a configuration that only includes a part for one ink (white ink in the present embodiment) among a plurality of color inks. In the present embodiment, as shown in FIG. 10, a tube for circulation 102 and a pump 103 are provided for the ink supply pipe 36.

An ink cartridge 100 (corresponding to a liquid tank) corresponds to each nozzle line of the head 31 and it is detachably mounted on a carriage 21. The ink cartridge 100 stores color ink corresponding to a nozzle line. The ink cartridge 100 in the present embodiment stores a white ink including a white pigment.

The ink supply pipe 36 supplies ink (here, it is white ink) from the ink cartridge 100 to the head 31. By the way, the ink supply pipe 36, which configures a flow channel of ink from the ink cartridge 100 to the nozzles Nz of the head 31, the common ink chamber 333, the ink supply opening 332, and the pressure chamber 331 (see FIG. 2A) correspond to a liquid supply channel.

When ink is not discharged from a nozzle, the tube for circulation 102 has a configuration having a circular channel that circulates ink of the ink supply pipe 36. One end of the tube for circulation 102 is connected to the upstream ($P_1$ point in the drawing) of an ink supply direction in the ink supply pipe 36, and the other end of the tube for circulation 102 is connected to the downstream ($P_2$ point in the drawing) in the ink supply direction in the ink supply pipe 36. By the way, it is not shown in the drawing, but $P_1$ point and $P_2$ point are respectively provided with a changeover valve that switches an ink flow channel. Also, a pump for stirring 103 is provided in the channel of the tube for circulation 102.

The pump 103 is used for circulating and stirring ink in an area between $P_1$ and $P_2$ of the ink supply pipe 36 through the tube for circulation 102 in a predetermined direction (direction shown in an arrow of a dotted line in the drawing). By the way, the tube for circulation 102 and the pump 103 correspond to the stirring part.

The controller 80 drives the pump 103 to circulate ink in a direction of an arrow shown in the drawing when a condition that ink is not discharged from the head 31 is beyond a certain period of time. Concretely, the ink is circulated in a path of $P_1$ point→the tube for circulation 102→the pump 103→the tube for circulation 102→$P_2$ point→the ink supply pipe 36→$P_1$ point. By circulating the ink as described, the ink in the area between $P_1$ point and $P_2$ point in the ink supply pipe 36 is stirred so that the ink is mixed and the concentration becomes even. On the other hand, when the ink is not discharged from the head 31 for a long time, in a position (bottom side of the drawing) of $P_3$ point which is closer to the nozzle plate 33b of the head 31, the ink concentration becomes high, and in a position (upper side of the drawing) which is closer to $P_2$ point, the ink concentration becomes low.

Because of this, by stirring ink, the ink supply pipe 36 between $P_1$ point and $P_2$ point becomes an area where the ink of the ink supply pipe 36 was stirred (hereinafter referred to as "stirred area"), and the ink supply pipe 36 from $P_2$ point to $P_3$ point which is the downstream side than the above area in an ink supply direction becomes an area where the ink of the ink supply pipe 36 is not stirred (hereinafter referred to as "unstirred area").

Because of this, after stirring, a predetermined amount of ink is ejected from the head 31, and it is necessary to substitute the stirred ink of the stirred area with the ink of the unstirred area. By this process, the even concentration of the ink can be ejected from the head 31, but the ink ejected from the head 31 is discarded through a waste fluid tube 65 (see FIG. 3).

If the ejection amount or the like varies when substituting, it may not be able to perform the substitution completely. In this case, the ink in the unstirred area (the ink concentration is high, or the ink concentration is low) may be ejected from the head 31 when printing.

Because of this, conventionally, it concerned a margin due to errors such as variability so that an extra substitution amount (ejection amount of ink) was set in advance. Specifically, an extra ejection amount of ink was set to certainly eject the ink in the unstirred area by the substitution. However, in this case, the ink of the stirred area (ink that becomes even concentration by stirring) may be unnecessarily ejected (discarded) without using for a print.

Thus, in the present embodiment, the substitution is completed immediately after ejecting the ink of the unstirred area so that the substitution is properly performed and the ejection amount (discard) of ink when the ink is substituted is reduced. Concretely, by using the detection result of the dot omission detection part 50, a timing of a substitution completion (completion of ink ejection) is determined. As described above, this is that in a case of a nozzle inspection by the dot omission detection part 50, a length of an ink column is varied in response to an ink viscosity (concentration) because an electric capacitance in the condenser of the nozzle plate 33b and the electrode for detection 613 is varied. Specifically, it is possible to estimate an ink viscosity from the change of the electric capacitance, and the substitution completion can be detected based on the estimated ink viscosity.

Substitution Process

Figure 11:
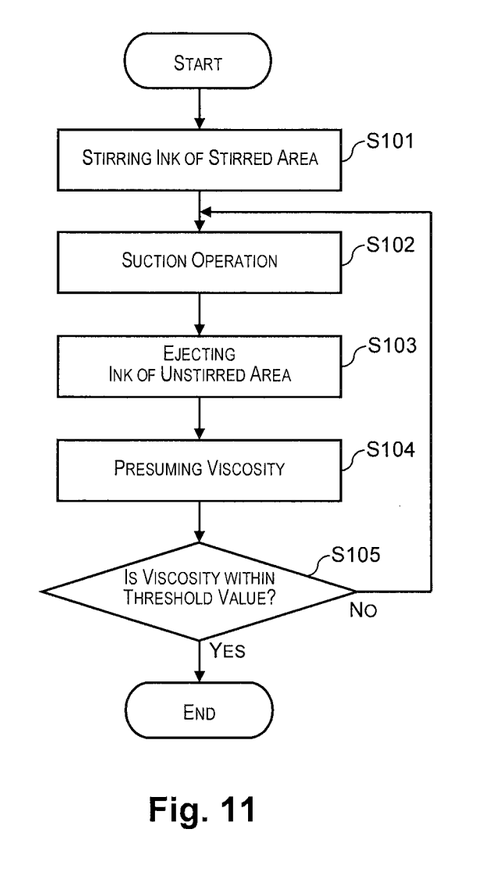
FIG. 11 is a flow diagram showing an operation of ink substitution process in the present embodiment.

FIG. 11 is a flow diagram showing an operation of ink substitution process in the present embodiment. Hereinafter, the substitution process of ink in the present embodiment will be explained with reference to FIG. 10.

First, when ink (e.g., white ink) is not discharged in a certain period of time, the controller 80 drives the pump 103 to circulate ink in an arrow direction of the dotted line in FIG. 10. By this process, the ink in the stirred area (area between $P_1$ point to $P_2$ point) of the ink supply pipe 36 is stirred (FIG. 11, S101). By the way, at this point, in the area between $P_2$ point and $P_3$ point (unstirred area), as it is closer to $P_3$ point, the concentration gradually becomes higher (the concentration becomes even).

After that, the controller 80 drives the cap mechanism 60 and performs a suction operation (S102). By this suction operation, the ink of the unstirred area, which is in a downstream side than the stirred area in an ink supply direction, is ejected (S103). Because of this, the ink of the stirred area is substituted with the ink of the unstirred area.

At this point, the controller 80 detects a change of an electric capacitance of an electrode between the nozzle plate 33b and the electrode for detection 613 by the dot omission detection part 50, and the ink viscosity is estimated based on the change of the electric capacitance (S104). And, it is judged whether or not the estimated viscosity is within the threshold value (S105). If the estimated viscosity is out of the threshold value (No in S105), it goes to Step S102 again, and if the estimated viscosity is within the threshold value (Yes in S105), the substitution process of ink is end.

Figure 12:
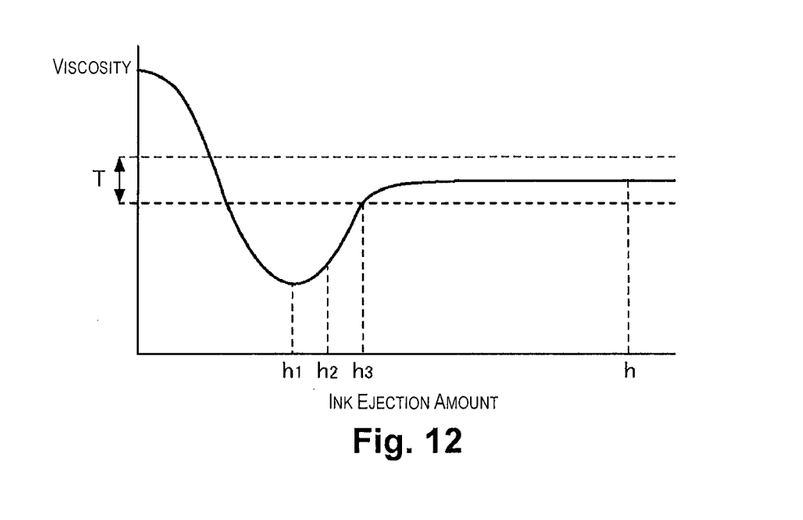
FIG. 12 is an explanatory diagram of a relationship between an ejection amount of ink and an ink viscosity.
Figure 13:
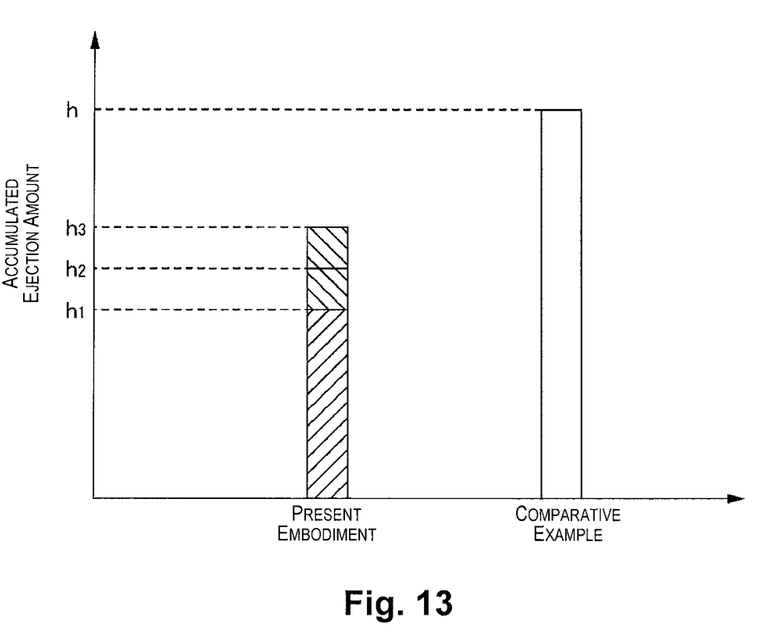
FIG. 13 is an explanatory diagram of a relationship between a number of ink ejections and an accumulated ejection amount.

FIG. 12 is an explanatory diagram of a relationship between an ejection amount of ink and an ink viscosity. The horizontal axis of the drawing shows the ejection amount of ink (accumulated ejection amount), and the vertical axis of the drawing shows an ink viscosity. Also, FIG. 13 is an explanatory diagram of a relationship between a number of ink ejections and an accumulated ejection amount. In FIGS. 12 and 13, h1, h2, and h3 are an ejection amount (an accumulated ejection amount) in each suction operation of the present embodiment, and h is a comparative example of the ejection amount.

In a case that ink is not discharged from the head 31 in a certain period of time in FIG. 10, after stirring the ink of the stirred area ($P_1$ point to $P_2$ point), FIG. 12 shows a change of the ink viscosity when the ink is ejected from the head 31. Also, an area showing the dotted lines in the drawing is the threshold value (threshold value T) of the ink viscosity which was set in advance. When a condition that ink is not discharged continues in FIG. 10, a concentration of an ink becomes high in a vicinity of nozzle (vicinity of $P_3$ point) of the head 31. Thus, a viscosity (left end of the drawing) of the first ejected ink from a nozzle by suction is quite larger that the threshold value T. And, the ink viscosity is reducing while ejecting the ink so that it becomes lower than the lower limit of the threshold value T. At this point, the ink to be ejected is the ink closer to the upper end (vicinity of $P_2$ point) of the unstirred area (downstream side than $P_2$ point in an ink supply direction). That is, it is a thin concentration ink. Because of this, when the ink of the unstirred area ($P_2$ point to $P_3$ point) is ejected, there is a part that the ink viscosity is in a range of the threshold value T so that in the first time of the ejection (suction operation), the ink of the ejection amount $h_1$ which is definitely over the threshold value T is ejected (the ink ejection amount is set larger than other suction times).

After that, as the ink is ejected, the ink viscosity gradually increases. In the present embodiment, the suction operation is performed with very little ejection amount after the second time ejection. From the drawing, after the second time ejection, the viscosity is lower than the lower limit of the threshold value T. And, after the next third time ejection, the viscosity is within the threshold value T. After that, the viscosity stabilizes approximately constant. This indicates that the ink stirred in the stirred area ($P_1$ point to $P_2$ point) is ejected from the nozzle.

As shown in FIG. 12 and FIG. 13, in the comparative example, the ink ejection amount including a margin is set to h so as to certainly discharge the ink of the unstirred area (it becomes within the range of the threshold value T, certainly). Thus, the ink in the stirred area (the ink that became even concentration by stirring) is also ejected. That is, even though it could properly use for printing, the ink amount that is discarded increases.

On the other hand, in the present embodiment, in the first suction operation, the ink is ejected in smaller ejection amount $h_1$ ($h_1 < h$) than the ejection amount h of the comparative example. However, the ejection amount $h_1$ is set in an adequate amount that the viscosity of the ink is less than the lower limit of the threshold value T. In the present embodiment, the ink is ejected by the suction so that an ejection amount is easily controlled. After the first suction operation, since the viscosity is lower than the lower limit of the threshold value T, the ink of the unstirred area (thin concentration ink) may be still remained.

In the second and subsequent suction operations, the ink is repeatedly ejected in an ejection amount smaller than the first time ejection amount $h_1$. For example, in the second time suction operation, the amount of ink corresponding to ($h_2 - h_1$) as shown in the drawing is ejected. Thus, the accumulated ejection amount becomes $h_2$ after the second suction operation. At this point, the viscosity is still less than the lower limit of the threshold value T so that the third suction operation is performed. After the third suction operation, the ejection amount becomes $h_3$ so that it is within a range of the threshold value T as shown in FIG. 12. When the controller 80 determines that the viscosity is within a range of the threshold value T, the ink discharge is end.

By this process, when the ink of the stirred area is substituted with the ink of the unstirred area, it can suppress that the ink of the stirred area is ejected from a nozzle. Therefore, the substitution is securely performed and it can suppress that the ink of the stirred area is unnecessarily ejected.

As described above, the printer 1 of the present embodiment comprise the head 31 that discharges ink (white ink) including a pigment (e.g., white color pigment), and the ink supply channel (the ink supply pipe 36, the common ink chamber 333, the ink supply opening 332, the pressure chamber 331) that supplies ink to a nozzle of the head 31 from the ink cartridge 100. Also, the printer 1 comprises the dot omission detection part 50 and the stirring part (the tube for circulation 102 and the pump 103) to stir the ink of the stirred area of the ink supply pipe 36. The ink discharged from the nozzle of the head 31 is changed to a ground potential by the nozzle plate 33b and then, the dot omission detection part 50 performs an inspection for a discharge state of the ink by discharging it toward the electrode for high voltage detection 613.

And, when the ink of the stirred area stirred by the stirring part is ejected from the head 31 to substitute with the ink of the unstirred area which is in the downstream side than the stirred area in the supply direction of the ink, the viscosity of the ink is estimated based on the change of the electrostatic capacitance detected by the dot omission detection part 50, and the controller 80 determines a timing of the substitution completion of the ink (in other words, ink ejection completion) based on the estimated viscosity.

By this configuration, when the unstirred part of the ink is substituted with the ink of the stirred part, ejection of the ink of the stirred area from the head 31 can be suppressed. Thus, the substitution is securely performed and the ejected ink amount (ink amount of the stirred area) by the substitution can be reduced.

Other Embodiments

The printer or the like is described as one embodiment, but the embodiment described above is intended to make the present invention easier to understand and should not be interpreted as limiting the present invention. The present invention can be modified and improved without deviating from the scope thereof, and the present invention includes equivalents thereof, as shall be apparent. The embodiment described hereinbelow in particular is included in the present invention.

Printer

A printer as one example of the liquid discharging device is described in the embodiment described above, but the invention is not limited to this example. For example, the same techniques of the present embodiment may be applied to various other liquid-discharging devices that use the inkjet technology, such as color filter manufacturing devices, dye devices, micromachining devices, semiconductor manufacturing devices, surface machining devices, three-dimensional modeling devices, gasifying and vaporizing devices, organic EL manufacturing devices (particularly macromolecular EL manufacturing devices), display manufacturing devices, film-forming devices, and DNA chip manufacturing devices.

Also, in the above embodiment, the printer 1 (so-called, serial printer) that alternately performs the image formation operation that discharges ink droplets while the head 31 is moving in a moving direction and the conveying operation that relatively moves the head 31 and the medium in a conveyance direction which intersects the moving direction is described as an example, but it is not limited. For example, it can be a printer (so-called, line printer) in which the heads (nozzles) are lined in a paper width direction that intersects the conveyance direction of the medium, and the ink is discharged toward a medium that conveyed below the heads so that an image is formed.

Discharge Method

In the above embodiment, the voltage element (piezo element) was used for the ink discharge. However, a method for discharging liquid is not limited to this. For example, other methods such as a method for generating bubbles in a nozzle by heating may be used.

Ink

The embodiment previously described was an embodiment of a printer so that ink was used, but the liquid discharged from the nozzles is not limited to such ink. For example, the nozzles may discharge liquids (including water) which include metal materials, organic materials (particularly macromolecular materials), magnetic materials, electroconductive materials, wiring materials, film-forming materials, electronic ink, machining liquids, gene solutions, and the like.

Also, in the above described embodiment, it describes the white ink including the white color pigment, but it is not limited to this. The same process may be performed to other color inks. By the way, in the white ink, the white color pigment (titanium oxide) is easily settled out so that when the white ink is used, it is especially effective. Also, ink including a substance having sedimentation properties other than the pigment may be used. In this case, as described in the above embodiment, by performing the stirring and the substitution, the ink ejection amount can be reduced.

Dot Omission Detection Part 50

In the above described embodiment, without providing a voltage-dividing circuit in the dot omission detection part 50, an abnormality of the electrode for detection 613 is detected based on the change of an electric state caused by the current If for discharge inspection, but it is not limited to this. The power voltage may be divided by the voltage-dividing circuit and an abnormality of the electrode for detection 613 may be detected based on the detected voltage.

Also, in the above described embodiment, the electrode for detection 613 is controlled to be a high potential than the nozzle surface, and the electric potential change of the electrode for detection 613 caused by discharging the ink droplet by the condenser for detection 54 was extracted, but it is not limited to this. For example, a high voltage power source unit is connected to the nozzle plate 33b to be a high potential, and the electrode for detection 613 is connected to the ground to be a ground potential. A dot omission nozzle may be detected by a potential change of the nozzle plate 33b, or a dot omission nozzle may be detected by a potential change of the electrode for detection 613. Also, in the electrode for detection 613 of the high potential and the nozzle plate 33b of the ground potential, a dot omission nozzle may be detected by a potential change of the nozzle plate 33b by the ink discharge.

In the above described embodiment, by making the nozzle plate to be the first potential (ground potential), the ink discharged from the nozzles is the ground potential, but it is not limited to this. If there is a configuration that the ink discharged from the nozzles becomes the first potential (ground potential), the nozzle plate may not be an electrode. For example, an ink flow channel, a pressure chamber 331, and the like may be provided in a wall surface. A conductive material that conducts with the ink in the ink nozzle may be provided and this conductive material may be a ground potential. Also, the ink is not limited to the ground potential, but it may be acceptable if there is a required potential difference for the detection in between the electrode for detection 613.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A liquid-discharging device comprising:
    a nozzle configured and arranged to discharge liquid including a substance having sedimentation properties;
    a liquid supply channel configured and arranged to supply the liquid to the nozzle from a liquid tank that stores the liquid;
    an inspection part configured and arranged to bring the liquid to be discharged from the nozzle to a first electric potential by a first electrode, to discharge the liquid toward a second electrode of a second electric potential which is different from the first electric potential, and to inspect a discharge state of the liquid based on a change of an electrostatic capacitance between the first electrode and the second electrode;
    a stirring part configured and arranged to stair the liquid in a predetermined area of the liquid supply channel; and
    a control part configured and arranged to cause the nozzle to eject the liquid in order to substitute the liquid in an area downstream side than the predetermined area with respect to a liquid supply direction with the liquid stirred by the stirring part in the predetermined area, the control part being configured to determine a timing of ejection completion of the liquid based on the change of the electrostatic capacitance detected by the inspection part.

2. The liquid-discharging device according to claim 1, wherein
    the control part is configured to estimate a viscosity of the liquid based on the change of the electrostatic capacitance, and to determine the timing of ejection completion of the liquid based on a result of estimation.

3. The liquid-discharging device according to claim 1, wherein
    the substance having sedimentation properties includes a pigment.

4. The liquid-discharging device according to claim 1, wherein
    the control part is configured to cause the nozzle to eject the liquid by suctioning.

5. A method for substituting liquid in a liquid-discharge device including a nozzle configured and arranged to discharge the liquid including a substance having sedimentation properties, and a liquid supply channel configured and arranged to supply the liquid to the nozzle from a liquid tank that stores the liquid, the method for substituting liquid comprising:
    stirring the liquid in a predetermined area of the liquid supply channel;
    ejecting the liquid from the nozzle in order to substitute the liquid in an area downstream side than the predetermined area with respect to a liquid supply direction with the liquid stirred in the predetermined area;
    inspecting a change of an electrostatic capacitance between a first electrode and a second electrode by bringing the liquid to be discharged from the nozzle to a first electric potential by the first electrode and discharging the liquid toward the second electrode of a second electric potential which is different from the first electric potential; and
    determining a timing of ejection completion of the liquid based on the change of the electrostatic capacitance.

* * * * *